US00PP33658P3

(12) United States Plant Patent
Jennings

(10) Patent No.: US PP33,658 P3
(45) Date of Patent: Nov. 23, 2021

(54) ***RUBUS* PLANT NAMED 'SKYE'**

(50) Latin Name: *Rubus idaeus*
Varietal Denomination: Skye

(71) Applicant: James Hutton Ltd., Dundee (GB)

(72) Inventor: Sophia N Jennings, Dundee (GB)

(73) Assignee: JAMES HUTTON LTD., Dundee (GB)

( * ) Notice: Subject to any disclaimer, the term of this patent is extended or adjusted under 35 U.S.C. 154(b) by 0 days.

(21) Appl. No.: 17/035,439

(22) Filed: Sep. 28, 2020

(65) Prior Publication Data

US 2021/0105924 P1 Apr. 8, 2021

(30) Foreign Application Priority Data

Oct. 8, 2019 (QZ) ..... PBR 2019/2567

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499
See application file for complete search history.

(56) References Cited

PUBLICATIONS

"New raspberry from GPG and James Hutton", www.fruitnet.com/fpj/article/181060/new-raspberry-from-gpg-and-james-hutton, published Mar. 4, 2020.*
Trademark to 'Skye', filed by Monrovia Nursery Company Corporation California, Sep. 10, 2019, serial No. 88610900.*
UPOV hit on *Rubus* plant named, 'Skye', QZ PBR 20192567, filed Oct. 9, 2019.*

* cited by examiner

*Primary Examiner* — Anne Marie Grunberg
(74) *Attorney, Agent, or Firm* — Penny J. Aguirre

(57) ABSTRACT

A new cultivar of *Rubus idaeus* plant named 'Skye' that is characterized by its canes that have thorns that are greyed-purple in color, its canes that require low chill hours to flower, its fruits that have a glossy surface, and its summer floricane fruit production and very late autumn primocane fruit production.

2 Drawing Sheets

Botanical classification: *Rubus idaeus.*
Cultivar designation: 'Skye'.

CROSS-REFERENCE TO A RELATED APPLICATION

This application claims priority to European Community Plant Variety Office (CPVO) Plant Breeder's Rights Application No. 2019/2567 filed on Oct. 8, 2019, under 35 U.S.C. 119(f), the entire contents of which is incorporated by reference herein.

BACKGROUND OF THE INVENTION

The present invention relates to a new and distinct cultivar of *Rubus idaeus* named 'Skye' and will be referred to hereinafter by its cultivar name, 'Skye'. 'Skye' is a new raspberry plant grown for fruit production.

The new cultivar was derived from a controlled breeding program in Dundee, Scotland, United Kingdom. The objectives of the breeding program are to develop new raspberry cultivars suitable for the fresh fruit market, both floricane and primocane, with high fruit quality, improved agronomic qualities and increased tolerance to pathogens.

The Inventor made a cross in spring of 2012 between an unnamed proprietary plants in the Inventor's breeding program, reference no. 0703F5 as the female parent and reference no. 0994H-12 as the male parent. The Inventor selected 'Skye' in spring of 2015 as a single unique plant amongst the seedlings that resulted from the above cross.

Asexual propagation by root cuttings and tissue culture using meristematic tissue has shown that the unique features of the new cultivar are stable and reproduced true to type in successive generations.

SUMMARY OF THE INVENTION

The following traits have been repeatedly observed and represent the characteristics of the new cultivar. These attributes in combination distinguish 'Skye' as a new and unique cultivar of *Rubus.*

1. 'Skye' exhibits canes that have thorns that are greyed-purple in color.
2. 'Skye' exhibits canes that require low chill hours to flower.
3. 'Skye' exhibits fruits that have a glossy surface.
4. 'Skye' exhibits early summer floricane fruit production and very late autumn primocane fruit production.

The seed parent of 'Skye' differs from 'Skye' in having canes that are spineless, having a high chill requirement, fruits that are smaller in size and dull in appearance. The pollen parent of 'Skye' differs from 'Skye' in having canes that have pink and green spines and fruits that are round in shape. 'Skye' can be compared to the *Rubus* cultivars 'Autumn Bliss' (U.S. Plant Pat. No. 6,597) and 'Glen Ample' (U.S. Plant Pat. No. 11,418). 'Autumn Bliss' is similar to 'Skye' in having an autumn primocane fruit production. 'Autumn Bliss' differs from 'Skye' in having fruit production very early in the season on the primocanes, is tolerant to *Phytophthora* root rot, does not plug from the receptacle easily when picking and has a shorter storage time post-harvest. 'Glen Ample' is similar to 'Skye' in producing fruit in the summer on floricanes. 'Glen Ample' differs from 'Skye' in having fruit that is produced mid-summer, canes that are spine free, fruit that is dull in appearance and in lacking fruit production in autumn.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website and facebook listings by James Hutton Ltd. and fruitnet.

BRIEF DESCRIPTION OF THE DRAWINGS

The accompanying colored photographs illustrate the overall appearance and distinct characteristics of the new *Rubus*. The photographs were taken of plants 24 months in age as as grown in a polytunnel in a 10-liter container in Dundee, Scotland, United Kingdom.

The photograph in FIG. 1 provides a view of developed and undeveloped fruit on a branch of 'Skye'.

Figure 1:
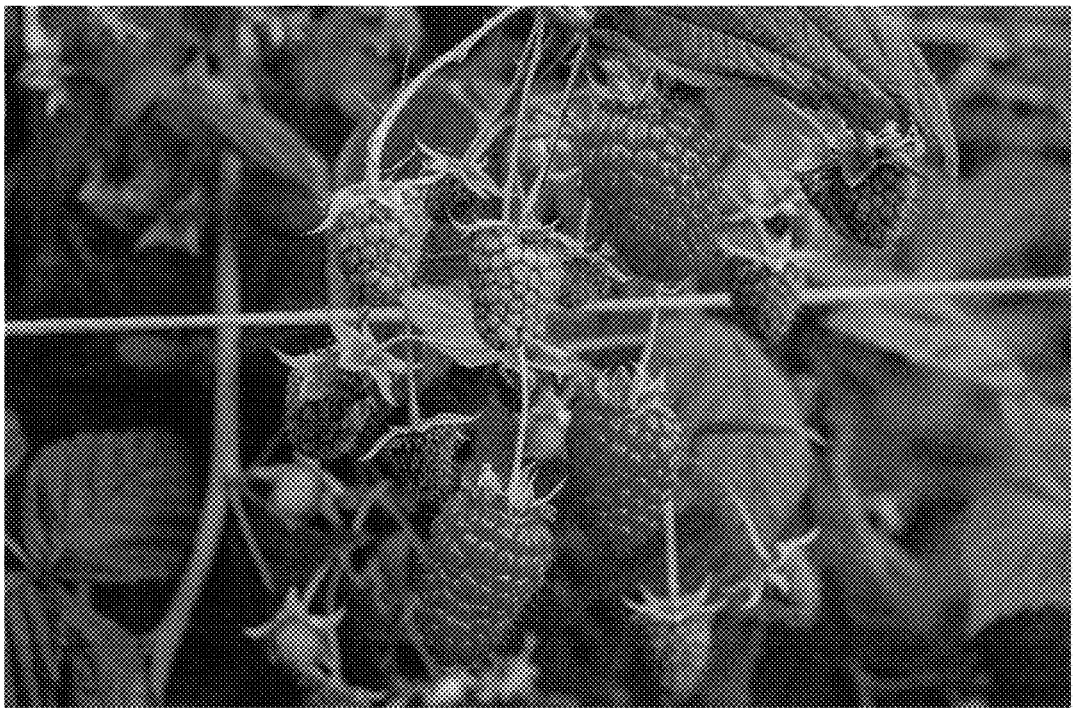
Figure 2:
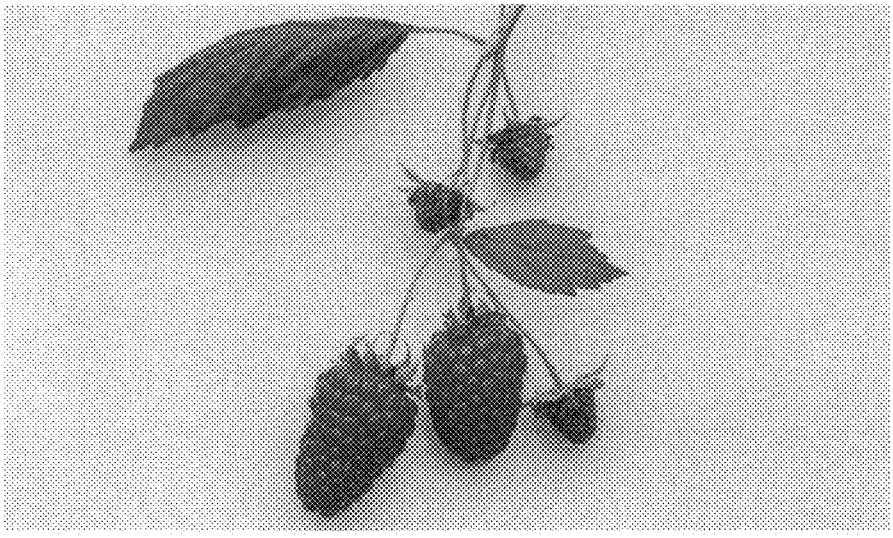

The photograph in FIG. 2 provides a close-up view of developed and undeveloped fruit on a branch of 'Skye'.

Figure 3:
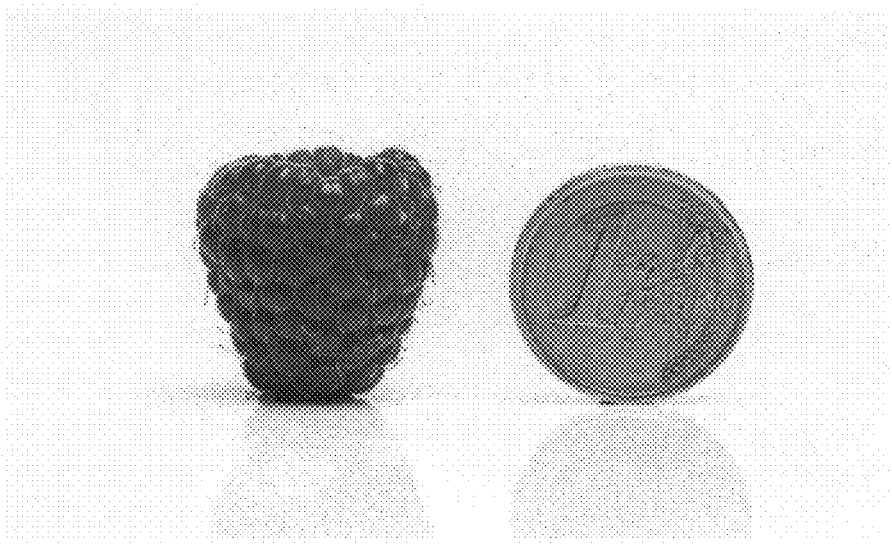

The photograph in FIG. 3 provides a close-up view of a single berry of 'Skye'.

The colors in the photographs are as close as possible with the photographic and printing technology utilized. The colors in the photographs may differ slightly from the color values cited in the detailed botanical description, which accurately describe the colors of the new *Rubus*.

DETAILED BOTANICAL DESCRIPTION OF THE PLANT

The following is a detailed description of plants 24 months in age as grown in a polytunnel in 10-liter containers in Dundee, Scotland, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Fruit is produced on the primocane in late autumn and also in the following summer on the remaining floricane, a 'double cropping' genotype.

*Plant habit.*—Upright with straight long canes.

*Height and spread.*—An average of 2.37 m in height and 22 cm in spread as grown in a 10-liter container.

*Hardiness.*—This trait has not been fully characterized in a range of cold weather climates, but the plants can successfully grow in western Europe (UK Hardiness Zone 7).

*Diseases and pests.*—Resistance to large raspberry aphid (*Amphorophora idaei*) and raspberry bushy dwarf virus (RBDV) after 4 years of testing.

*Root description.*—Vigorous root, prolific spawn production.

*Branching habit.*—None.

*Propagation.*—Root cuttings or tissue culture.

*Root development.*—An average of 2 weeks to initiate roots, an average of 6 months to fully develop as a plant with 3 canes that are 2 m in height.

*Growth rate.*—Moderate.

Cane description

*Cane size.*—An average of 2.37 m in length and an average of 11.2 mm in width.

*Cane internode length.*—Up to 6.1 cm.

*Cane shape and aspect.*—Angled.

*Cane strength.*—Moderately strong to strong.

*Cane color.*—New canes; 144B and heavily suffused with 186A, mature canes; 165A with internodes 165A.

*Thorns.*—1 mm in length with base 2 mm in length and 1 mm in width, 187A in color, distance between spines ranging between 1 mm to 3 mm in length.

*Stem surface.*—Glabrous with spines.

*Stipules.*—2 per petiole, leafy; narrowly elliptic in shape, an average of 7.2 mm in length and >1 mm in width, apex narrowly acute, cuneate base, upper and lower surface color 144C.

*Primocane.*—Develops in late spring and initiates flower buds in late summer and develops fruit in year 1 on the top 30% of cane.

Foliage description:

*Time of vegetative bud burst.*—Early season (early March in Scotland, United Kingdom).

*Vegetative bud size.*—An average of 3.8 mm in length and 2.2 mm in width on current year's growth.

*Leaf shape.*—Ovate to rhomboid.

*Leaf arrangement.*—1 terminal and 1 to 2 lateral pairs.

*Leaf division.*—1 to 3.

*Leaf attachment.*—Petiolate.

*Leaf orientation.*—Flat to pendant.

*Leaf size.*—An average of 14.7 cm in length and 20 cm in width.

*Leaflet shape.*—Ovate and rhomboid.

*Leaflet base.*—Ranging between ovate, deltoid and rhomboid.

*Leaflet apex.*—Acute.

*Leaflet venation.*—Pinnate, primarily matches leaf color on upper surface and lower surface.

*Leaflet margins.*—Serrate.

*Leaflet arrangement.*—1 terminal and 1 to 2 lateral pairs.

*Leaflet attachment.*—Primarily sessile.

*Relative position of lateral leaflet.*—Non-overlapping to slightly overlapping at base.

*Profile of leaflet cross-section.*—Slightly concave.

*Leaflet surface.*—Upper and lower surface rugose, spine along lower side of mid-rib on lower surface of terminal leaflet 1 mm in length.

*Leaflet color.*—Young; upper surface 134A, lower surface 143D, mature; upper surface 144A, lower surface 143D, no change in autumn.

*Leaflet size.*—Terminal leaflet; an average of 13.1 cm in length and 16.9 cm in width.

*Petioles.*—Round in shape, an average of 5.5 cm in length and 2 mm in width, upper surface 144B, suffused with 181C, lower surface 144D, strong.

*Rachis.*—Round in shape, an average of 3.25 cm in length and 2 mm in width on lower laterals and 1.5 cm in length and 2 mm in width on upper laterals, upper surface 144B, lower surface 144D, occasional spines 1 mm in length and 185A in color.

Inflorescence description:

*Blooming period.*—Primocanes flower late August to late September for 5 weeks, floricanes flower late May to early July for 5 weeks in Scotland, United Kingdom.

*Inflorescence.*—Panicle, upper plant an average of 36.1 cm in length, lower plant 23.25 cm in length.

*Peduncle.*—Oval in shape, an average of 1.8 cm in length and 1.5 mm in width, upright habit, color upper surface 53A, color lower surface 142C.

*Pedicels.*—Round in shape, 53A in color, an average of 1.7 cm in length and 1 to 2 mm in width, strong in strength, held in multiple angles between 90° to 180° to peduncle.

*Flower buds.*—Nearly orbicular in shape, average of 7 mm in length and 6.4 mm in diameter, color; immature sepals 144A to 144B, petals NN155D, surface petal portion glabrous.

*Flower type.*—Spreading calyx with center of numerous stamens and with numerous pistols, petals quickly shed upon opening.

*Flower number.*—An average of 20 to 27 flowers per lateral.

*Flower fragrance*—None.

*Flower size.*—Average of 5 mm in height and 7 mm in diameter.

*Sepals.*—5, an average of 6 mm in length and 5 mm in width, broadly ovate to near deltoid in shape, base broad cuneate, apex aristate, entire margin, color when opening and mature 144B on upper surface and 143C on lower surface.

*Petals.*—5, an average of 7 mm in length, 3 mm in width, base cuneate, apex obtuse, entire margin with medium undulation, glabrous and matte on upper and lower surfaces, color; when opening and fully open upper and lower surface NN155D.

*Bracts.*—Ovate at base of pedicel, leafy; narrow elliptic in shape, an average of 10.8 cm in length and 1.2 cm in width, apex narrow acute, cuneate base, entire margin, color both surfaces 144A.

*Androecium.*—Stamens; an average of 93, filaments; 3 mm in length, NN155D in color, anthers; 1 mm in length, >1 mm in width, 11C in color, pollen; moderate in quantity.

*Gynoecium.*—Pistils; 110, average of 5 to 7 mm in length, stigmas; cup-shaped, >1 mm in length and diameter, 11C in color, style; 4 mm in length, 11C in color, ovary; 11C in color.

Fruit description:

*Fruit number.*—An average of 18 to 25 per lateral.

*Fruit size.*—An average of 3.4 cm in length and 2.4 cm in diameter.

*Fruit shape.*—Broad conical.

*Fruit texture.*—Slightly dry and smooth, not seedy.

*Fruit color.*—A blend of 187B and 187C.

*Fruit adherence to plug.*—Medium.

*Fruit firmness.*—Medium to high.

*Druplets.*—An average of 134 per berry, 6 mm in length and 4 mm in width.

*Seed.*—Reniform in shape, average of 77 per fruit, 2.8 mm in length, 1 mm in width, 27D in color.

*Cropping frequency.*—Annually, on floricanes and primocanes.

*Harvest dates.*—Typically a first harvest date of 4$^{st}$ of October and a last harvest date of the 4th November (primocane), 10th of July to the 15th of August (floricane).

*Flavor.*—Sweet with low acidity, fruity aroma.

*Fruit weight.*—6.5 g/fruit (Primocane).

*Brix.*—10.5° to 12°.

*Titratable acidity.*—8.2%.

*Shelf life.*—An average of 7 to 10 days after picking.

*Market use.*—Fresh fruit.

It is claimed:

1. A new and distinct cultivar of *Rubus idaeus* plant named 'Skye' as herein illustrated and described.

* * * * *